United States Patent [19]

Love et al.

[11] Patent Number: 5,489,296
[45] Date of Patent: Feb. 6, 1996

[54] HEART VALVE MEASUREMENT TOOL

[75] Inventors: Charles S. Love, Newbury Park; Jack W. Love, Santa Barbara, both of Calif.

[73] Assignee: Autogenics, Newbury, Calif.

[21] Appl. No.: 169,618

[22] Filed: Dec. 17, 1993

[51] Int. Cl.⁶ .................................................. A61F 2/24
[52] U.S. Cl. .............................. 623/2; 623/900; 128/774
[58] Field of Search ..................... 128/774; 623/2, 623/66, 900, 901; 137/515.7

[56] References Cited

U.S. PATENT DOCUMENTS

| | | | |
|---|---|---|---|
| 3,513,485 | 5/1970 | Davila | 623/2 |
| 3,548,418 | 12/1990 | Angell et al. . | |
| 4,211,241 | 7/1980 | Kaster et al. . | |
| 4,211,325 | 7/1980 | Wright | 623/2 X |
| 4,247,292 | 1/1981 | Angell . | |
| 4,470,157 | 9/1984 | Love . | |
| 4,585,453 | 4/1986 | Martin et al. | 623/2 |
| 4,679,556 | 7/1987 | Lubock et al. . | |
| 4,705,516 | 11/1987 | Barone et al. | 623/2 |
| 5,156,955 | 11/1992 | Love et al. . | |
| 5,236,450 | 8/1993 | Scott | 623/2 |
| 5,326,371 | 7/1994 | Love et al. | 623/2 |

FOREIGN PATENT DOCUMENTS

92/03990  3/1992  WIPO .......................................  623/2

OTHER PUBLICATIONS

"Rapid Intraoperative Fabrication of an Autogenous Tissue Heart Valve: A New Technique", Love et al.
"A Fascia Lata Mitral Valve Based on the 'frustrum' Principle", Brownlee et al., Guy's Hospital, London, Thorax (1971), 26, 284.
"A Method for Preparing and Inserting a Homograft Aortic Valve", Barratt-Boyes, Cardiothoracic Surgical Unit, Green Lane Hospital, Auckland, New Zealand.

*Primary Examiner*—Sam Rimell
*Attorney, Agent, or Firm*—Knobbe, Martens, Olson & Bear

[57] ABSTRACT

The present invention provides a heart valve measurement tool in the form of an obturator. The obturator is specifically configured to measure the size of the annulus of the heart to be fitted with a prosthetic heart valve. A plurality of obturators of varying sizes are utilized to determine the appropriate valve size.

15 Claims, 4 Drawing Sheets

HEART VALVE MEASUREMENT TOOL

FIELD OF THE INVENTION

This invention relates to heart valve measurement tools and, in particular, to improved obturators which are specifically configured to measure the size of the annulus of the heart to be fitted with a prosthetic heart valve and the method of using the obturators.

BACKGROUND OF THE INVENTION

Replacement of diseased or malfunctioning heart valves requires that the replacement valve be appropriately sized to fit the annulus of the valve that is being replaced. In order to determine the required valve size, the patient's valve annulus needs to be measured. One method of measuring the valve annulus includes taking X-rays of the patient's heart and measuring the diameter of the annulus from the X-rays. However, due to the inaccuracies of X-rays, this method is not very reliable and only an approximate estimate of the valve annulus sizes can be made.

Another method of measuring the valve annulus involves the use of calipers and the like to measure the valve diameter. This method requires that the measurement be made by the surgeon during the valve-replacement procedure. Once the annulus diameter is measured, the valve annulus circumference is calculated and, subsequently, the appropriately-sized replacement valve is determined. This method, however, has several disadvantages. Due to the limited amount of space in the heart, it is difficult to properly located the measurement tools within the heart at the site of the annulus. In addition, a human valve annulus is not perfectly round or circular and, therefore, calculations of valve annulus circumference are imprecise.

U.S. Pat. No. 5,163,955 assigned to Autogenics, assignee of the present invention, describes improved tools for sizing the annulus by use of a series of sized obturators.

Therefore, there is a need for a heart valve annulus measurement device and method whereby a patient's valve annulus may be accurately measured to determine the appropriate replacement valve size. In addition, the device or method should facilitate valve annulus measurement so that the measurement may be performed in a time-efficient manner.

SUMMARY OF THE INVENTION

The present invention provides a device that is used during heart-valve replacement to measure the size of the annulus of the heart. During valve-replacement surgery, the diseased or malfunctioning heart valve is removed from the patient. The prosthetic replacement valve, having a base with predetermined circumference, is implanted at the valve annulus. The obturators of the present invention are improvements over those disclosed in the '955 patent and provide the necessary valve annulus measurements in order to implant the appropriately sized replacement valve.

The preferred embodiment of the present invention comprises a plug or obturator which is configured in a plurality of different sizes. The shape of the obturator closely resembles the shape of the replacement valve and the annulus of the heart. Each obturator has several predetermined dimensions which are used to accurately measure the annulus of the heart so that the appropriate size for the replacement valve may be determined.

The obturator is comprised of four sections. The first section has a threaded center-hole where a handle can be screwed into the obturator. The handle is used to push the obturator into the valve annulus. The second section is comprised of outwardly-tapered walls and includes the bottom portion of the threaded center-hole. The third section of the obturator corresponds to the base-piece of the replacement valve. Thus, the first, second and third sections of the obturator are configured to closely resemble the replacement prosthetic heart valve.

The fourth section of the obturator corresponds to the patient's heart valve in-flow diameter. Additionally, the four section is used to probe the annulus to determine whether there are any obstructions.

In use, a surgeon or technician successively plugs the annulus of the heart with the various-sized obturators until the appropriately sized obturator is determined. In addition to determining that the obturator fits securely into the patient's annulus, the surgeon or technician must also visually inspect the fit of the third section of the obturator. If the third section rests above or on top of the annulus, then the obturator is the correct size for the annulus. Thus, by utilizing the obturator, the appropriately sized prosthetic replacement heart valve is determined.

DETAILED DESCRIPTION OF THE INVENTION

The obturator 10 shown in the FIGURES is used to size the annulus of the heart valve to be fitted with a prosthetic heart valve 50. Once the valve annulus size is determined, the corresponding appropriately sized prosthetic heart valve 50 is implanted in the patient's heart. A significant feature of the preferred embodiment of this invention is that the obturator is configured to resemble both the replacement prosthetic heart valve and the annulus of the human heart.

Figure 1:
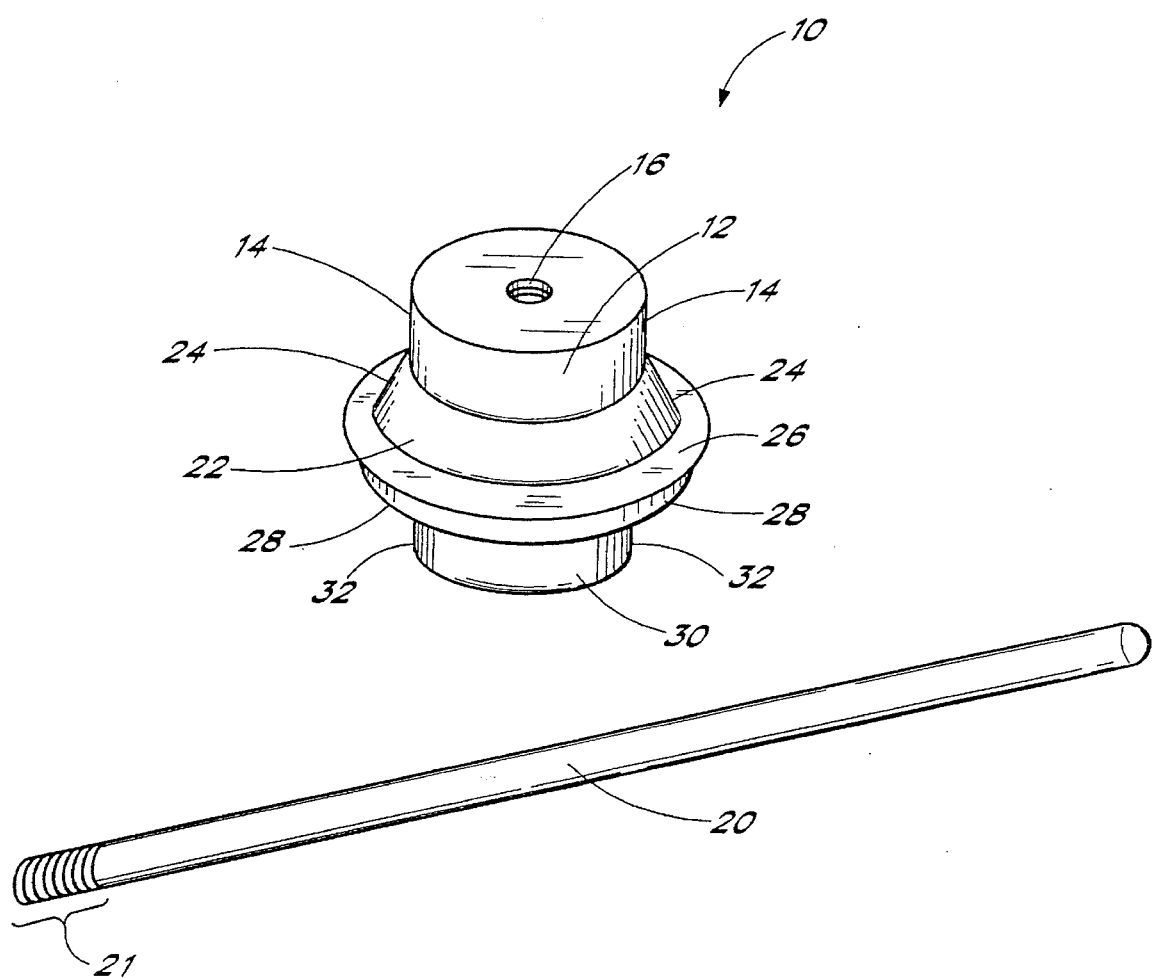
FIG. 1 is a perspective view of the obturator of the present invention.
Figure 2:
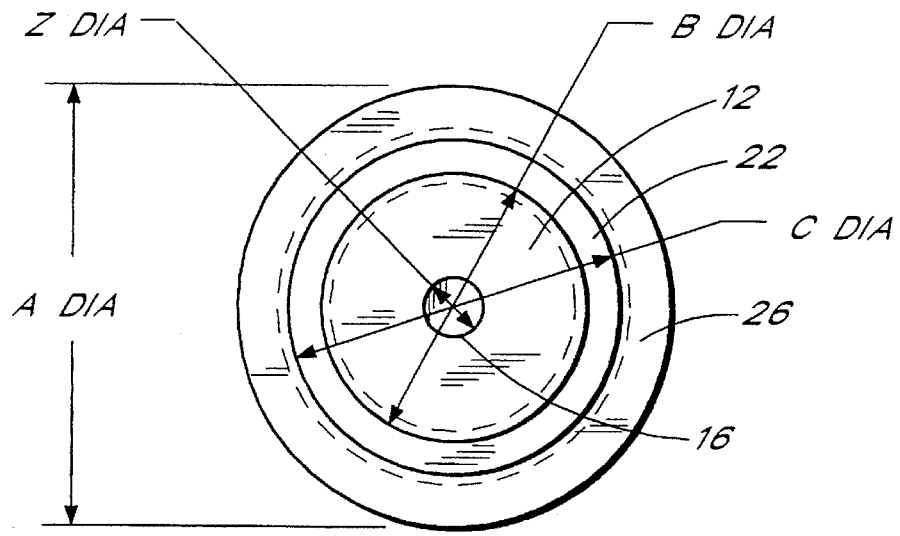
FIG. 2 is a cross-sectional top view of the device of FIG. 1.
Figure 3:
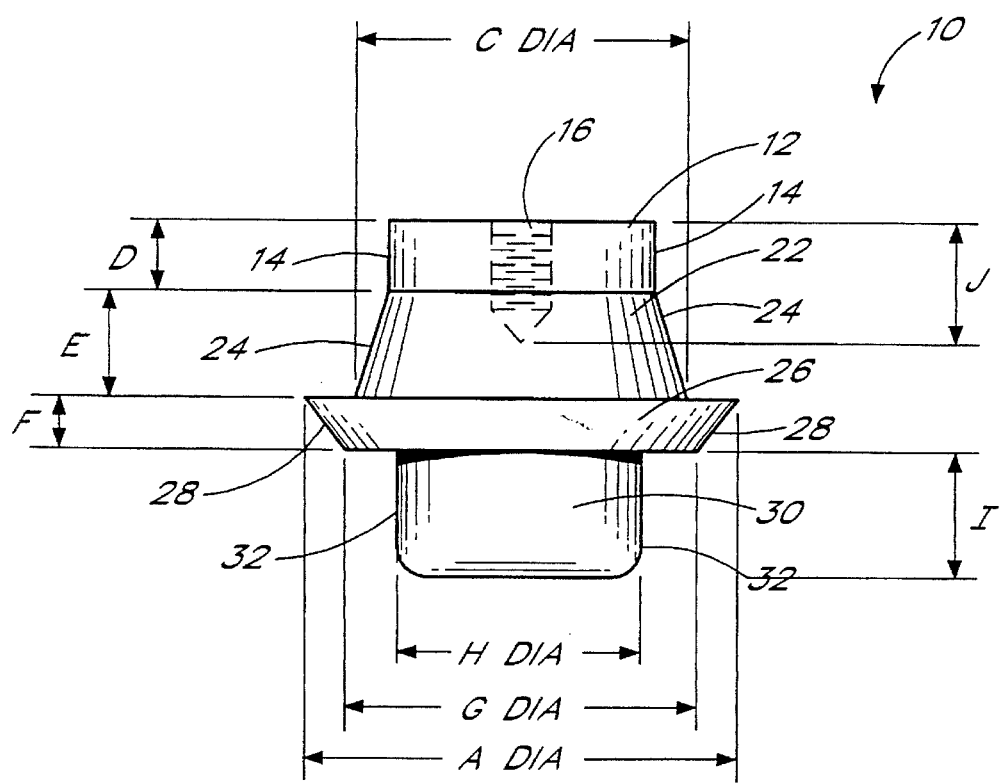
FIG. 3 is a cross-sectional side view of the device of FIG. 1.
Figure 4:
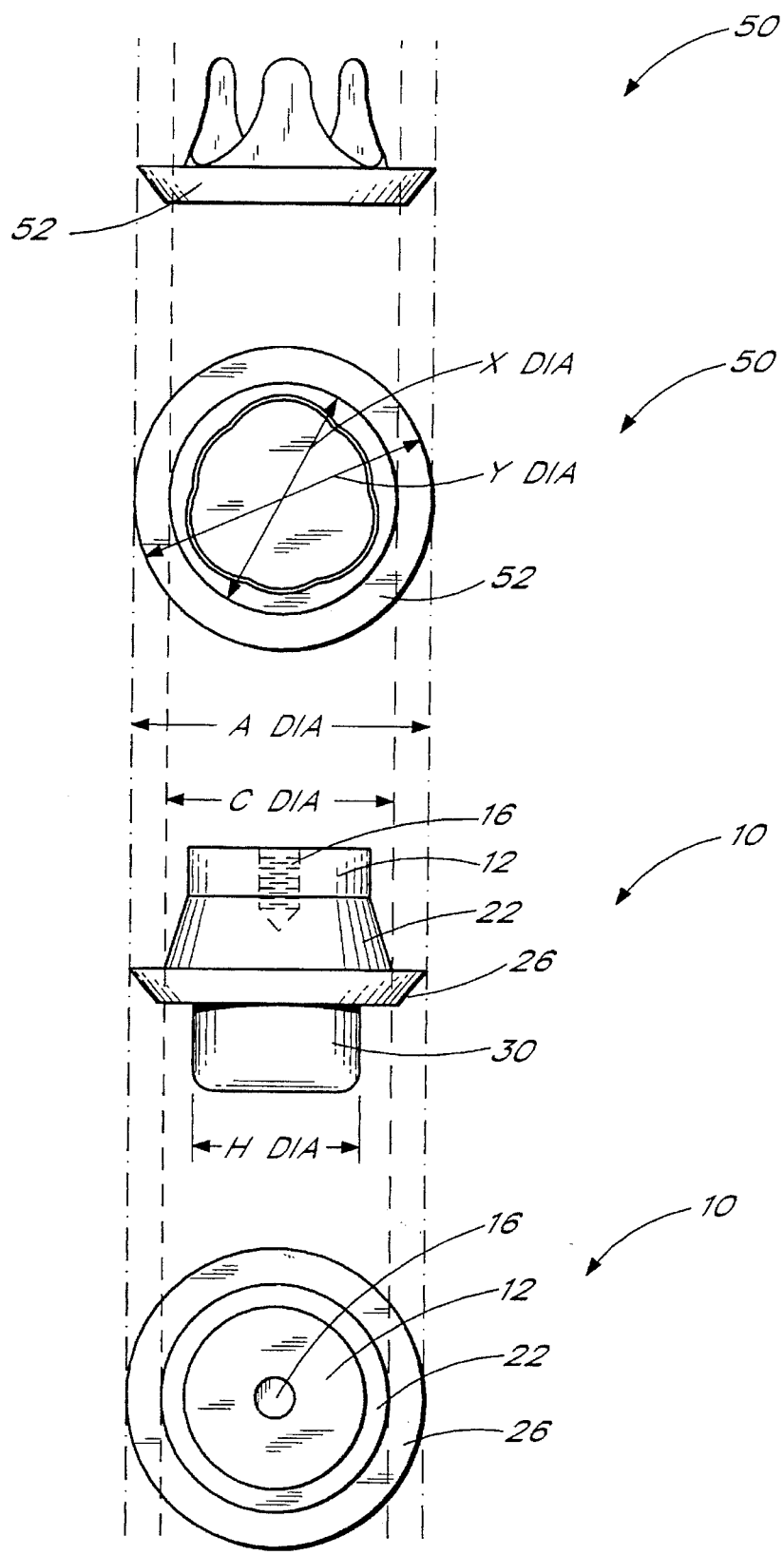
FIG. 4 illustrates both cross-sectional top and side views of a replacement valve and the obturator of FIGS. 2 and 3.

As shown in FIG. 4, each section of obturator 10 has predetermined heights and diameters that correspond to the various diameters and heights of a prosthetic heart valve 50. Referring to FIGS. 1–3, the first section 12 of the obturator 10 has the shape of a solid cylinder and is comprised of vertical walls 14 and an internally threaded hole 16 located along the axis at the center of the cylinder. The diameter "Z" of the threaded hole 16 is appropriately sized so as to mate with a handle 20. The diameter of the first section 12 is defined as "B" and its height is defined as "D".

The second section 22 of the obturator 10 has the shape of an upright solid cone frustum, having a height defined as "E". The second section 22 is comprised of outwardly tapered walls 24, wherein the uppermost cross-sectional diameter formed by the walls 24 of the second section 22 is equal to that formed by the walls 14 of the first section 12. Thus, the small diameter of the second section is also designated by the letter "B". The large diameter formed by the walls 24 is defined as "C". The threaded hole 16 of the first section 12 continues into a portion of the second section 22, along the axis of the second section 22.

Still referring to FIGS. 1–3, the third section 26 of the obturator 10 has inwardly-tapered walls 28, having the shape of an inverted solid cone frustum. The large diameter formed by the walls 28 of the third section 26 is adjacent to the large diameter of the second section 22. The third section 26 has small and large diameters designated by the letters "G" and "A", respectively. The height of the third section 26 is defined as "F".

The fourth section 30 of the obturator 10 of the present invention has the shape of a solid cylinder. The fourth section 30 is formed by vertical walls 32, similar to those of the first section 12. The diameter of the cylinder of the fourth section 30 is defined as "H" and is smaller than the diameter of the first section 12.

The obturator 10 is advantageously formed of a plastic, biocompatible material, such as Polysulfone. Other materials, which provide a rigid structure that is non-deformable upon insertion of the obturator 10 into the heart valve annulus, may also be used.

The obturator 10 is configured to resemble the prosthetic heart valve 50 and the annulus of the heart. Several dimensions of the obturator 10 correspond to those of a predetermined size prosthetic heart valve 50. For example, referring to FIG. 4, the large diameter "C" of the second section 22 of the obturator 10 corresponds to the inner-diameter "X" of the base-piece 52 of the replacement valve 50. In addition, the large diameter "A" of the third section 26 of the obturator 10 corresponds to the outer-diameter "Y" of the base-piece 52 of the replacement valve 50. These dimensional similarities aid the surgeon or technician in determining the appropriate size for the replacement valve for the annulus of the heart.

Referring to FIGS. 2 and 3, certain other dimensions of the obturator 10 are advantageously held constant, regardless of the size of the obturator 10. The first such dimension is the height "I" of the fourth section 30. As described below, the fourth section 30 is inserted into the annulus formed by excising the patient's natural valve. The depth of section 30 probes the annulus to determine whether there are any obstructions; therefore, a substantially constant depth of this section is desirable for all sizes of obturators regardless of their annulus opening size. The second dimension, which is advantageously held constant, is the diameter "Z" of the threaded hole 16. As a result, a single handle 20 can be used for any and all of the sized obturators. The third and final constant dimension is the height or depth "J" of the hole 16. This dimension ensures that a sufficient length of the threaded handle 20 can be screwed into each obturator 10. These dimensions are thus arbitrary and remain constant regardless of valve size, since valve sizing is not dependent upon these obturator dimensions.

Figure 5:
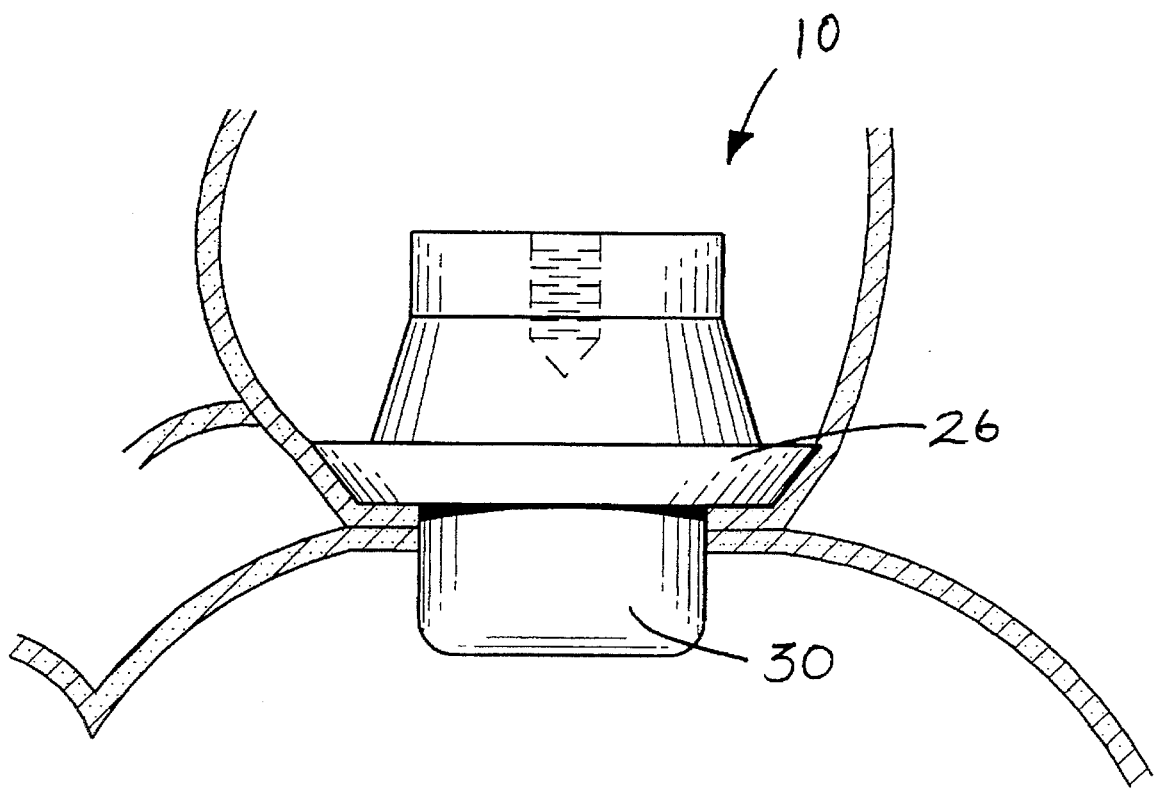
FIG. 5 is a cross-sectional view of the obturator of FIG. 1 seated within the annulus of a heart.

The method of using the obturator 10 of the present invention is as follows. During the heart valve replacement procedure, it will be understood that the surgeon or technician is provided with a plurality of obturator 10 sizes. As described in the '955 patent, these obturators are advantageously arranged in a first kit including the common handle 20. The surgeon or technician screws the handle 20, having an externally threaded section 21, into the threaded hole 16 of one of the obturators 10 and plugs the obturator 10 into the annulus of the patient's heart. If the obturator 10 securely fits into the annulus, as shown in FIG. 5, the obturator dimension or size is noted and the appropriately sized replacement valve 50 is determined. If, however, the obturator 10 does not fit within the annulus of the heart, the surgeon or technician successively plugs the annulus of the heart with the obturators 10 until the appropriate size of the annulus is determined.

The determination of a secure fit is, to some extent, based upon the individual surgeon's or technician's judgement and experience. However, certain requirements must be satisfied in order to ensure an appropriate fit. One requirement is that the valve annulus is free from obstruction. This requirement is satisfied by sliding the fourth section 30 of the obturator 10 completely into the annulus of the heart so that the third section 26 of the obturator 10 rests on the walls of the annulus, as shown in FIG. 5. Thus, one may assume that the annulus is sufficiently free from obstructions.

An additional requirement is that the fourth section of the obturator can be easily placed inside the collapsed annulus. If the fourth section of the obturator is too large, the surgeon or technician will experience great difficulty in fitting the obturator into the annulus of the heart. If, however, the fourth section easily fits within the annulus, the surgeon or technician must next determine if the fourth section is too small.

Proper sizing of the replacement prosthetic heart valve is very important. A particular feature of this invention is that it notifies the surgeon during the sizing procedure that a particular valve may be too small, notwithstanding that the fourth section 30 of the obturator 10 seems to properly fit within the open annulus of the heart. This is accomplished by visually inspecting the fit of the inverted cone frustum third section 26 of the obturator 10 to the annulus of the heart. If any portion of the inverted cone frustum section 26 of the obturator 10 fits within the open annulus of the heart, then the obturator 10, and subsequently the replacement valve, is too small and the surgeon is advised to test a larger obturator 10. However, if the inverted cone frustum section 26 of the obturator 10 rests above or on top of the annulus, as shown in FIG. 5, then the obturator 10 is the correct size for the annulus. From this measurement, the surgeon or technician can then obtain the appropriately sized replacement valve.

It should be appreciated that a range of obturator sizes corresponds to the various annulus sizes of the heart. For example, replacement of the mitral or atrioventricular valve utilizes a set of obturators ranging in size from 23 mm to 31 mm. For the aortic or pulmonary valves, obturator sizes may vary within the range of 19 mm through 29 mm. Replacement of valves in young children may require valves as small as 14 mm.

Obviously, numerous variations and modifications can be made without departing from the spirit of the present invention. Therefore, it should be clearly understood that the forms of the present invention described above and shown in the figures of the accompanying drawings are illustrative only and are not intended to limit the scope of the present invention.

What is claimed is:

1. An obturator for measuring the size of a valve annulus in a human heart prior to the implantation of a bioprosthetic replacement heart valve having a base portion with inflow, inner and outer diameters into said heart, said obturator threadably engageable with a handle for insertion into the annulus of a human heart, said obturator comprising:

a first section having a generally cylindrical shape and a threaded hole drilled through its center;

a second section having the shape of a conical frustum;

a third section having the shape of an inverted conical frustum; and a fourth section having a generally cylindrical shape.

2. The obturator of claim 1, wherein said obturator is comprised of a plastic, biocompatible material.

3. The obturator of claim 2, wherein said material is Polysulfone.

4. The obturator of claim 1, wherein the configuration of said first, second and third sections of said obturator resembles a prosthetic replacement heart valve.

5. A method for measuring the size of an annulus of a patient's heart prior to the implantation of a bioprosthetic heart valve, said valve including a base portion having inflow, inner, and outer diameters, said method comprising the steps of:

providing a plurality of obturators, each of said obturators having a first section with a generally cylindrical shape and a threaded hole drilled through its center, a second section having the shape of a conical frustum and having upper and lower diameters, said lower diameter substantially equal to the inner diameter of the base of said bioprosthetic heart valve, a third section having the shape of an inverted conical frustum and having upper and lower diameters, said lower diameter substantially equal to the outer diameter of the base of said bioprosthetic heart valve and a fourth section having a generally cylindrical shape, the diameter of said fourth section being substantially equal to the inflow diameter of said bioprosthetic heart valve, each of said obturators having differing dimensions;

providing a handle having an externally threaded section;

threadably engaging said handle with one of said obturators;

inserting said obturator into the vascular annulus of said patient utilizing said handle;

determining whether said obturator fits within the vascular annulus of said patient;

disengaging and threadably engaging another of said obturators with said handle if said obturator does not fit within the vascular annulus of said patient until a fit is achieved with the vascular annulus of said patient, said method allowing the quick and accurate determination of the size of the vascular annulus of said patient during replacement of a diseased heart valve in said patient.

6. The method of claim 5, wherein said inserting step further comprises sliding said fourth section of said obturator completely into the annulus of the heart so that said third section of the obturator rests on top of the walls of the annulus.

7. The method of claim 5, wherein said inserting step includes verifying that said annulus is sufficiently free form obstructions.

8. The method of claim 5, wherein said determining step further comprises visually inspecting the fit of said third section of said obturator to the annulus of the heart.

9. The method of claim 5, wherein said disengaging step includes replacing said first obturator with a differently sized second obturator.

10. The method of claim 9, wherein said replacing step further includes utilizing a larger sized obturator for said second obturator if said first obturator is too small.

11. The method of claim 9, wherein said replacing step further includes utilizing a smaller sized obturator for said second obturator if said first obturator is too large.

12. An obturator for measuring the size of an annulus formed in a human heart after a patient's valve has been excised, said obturator comprising:

an inverted conical frustum having a first surface having a first diameter and a second surface having a second diameter, said first diameter being larger than said second diameter; and a generally cylindrical section integral with a portion of the second surface of said inverted conical frustum, the second diameter of the second surface of said inverted conical frustum being larger than a diameter of said generally cylindrical section so that the second surface of said inverted conical frustum rests on the walls of the annulus when said generally cylindrical section is inserted into the annulus.

13. A method for measuring the size of an annulus of a patient's valve prior to the implantation of a bioprosthetic heart valve, said method comprising the steps of:

inserting one or more cylinders into the annulus until a cylinder is found having a diameter substantially corresponding to the diameter of the annulus;

pushing said selected cylinder into the annulus until an inverted conical frustum integral with said selected cylinder prevents further ingress of said selected cylinder, said inverted conical frustum having a minimum diameter larger than the diameter of said selected cylinder; and determining whether any portion of said inverted conical frustum fits within the annulus to thus avoid selecting a valve size which is too small for the patient undergoing surgery.

14. A method for measuring the size of an annulus of a patient's valve prior to the implantation of a bioprosthetic heart valve, said method comprising the steps of:

providing a plurality of obturators, each of said obturators having a first section with a generally cylindrical shape and a hole drilled through its center, a second section having the shape of a conical frustum, a third section having the shape of an inverted conical frustum, and a fourth section having a generally cylindrical shape, the fourth section being integral with and smaller in diameter than an adjacent surface of said inverted conical frustum, each of said obturators having differently dimensioned first, second, third and fourth sections;

providing a handle;

engaging said handle with one of said obturators;

inserting said one of said obturators into the annulus using said handle, sequentially repeating said insertion with each remaining of said obturators engaged with said handle until an obturator is found in which its fourth section has a diameter substantially corresponding to the diameter of the annulus;

visually inspecting the first, second and third sections of said selected obturator, corresponding to the bioprosthetic valve configuration; and determining whether the third section of said selected obturator fits appropriately on the valve annulus so that the appropriately sized valve is selected.

15. A plurality of obturators for measuring the size of a valve annulus in a human heart prior to the implantation of a bioprosthetic replacement heart valve having a base portion with inflow, inner and outer diameters into said heart, each obturator of said plurality being engageable with a handle for insertion into the annulus of said heart, each obturator of said plurality comprising:

a first section having a generally cylindrical shape and a hole drilled through its center;

a second section having the shape of conical frustum;

a third section having the shape of an inverted conical frustum; and a fourth section having a generally cylindrical shape;

wherein said obturators are manufactured in a plurality of sizes.

* * * * *